US00PP17219P2

(12) United States Plant Patent
Dirr

(10) Patent No.: US PP17,219 P2
(45) Date of Patent: Nov. 14, 2006

(54) CRAPEMYRTLE PLANT NAMED 'GAMAD IV'

(50) Latin Name: *Lagerstroemia indicia×L. fauriei*
Varietal Denomination: Gamad IV

(75) Inventor: Michael A. Dirr, Bogart, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 11/204,762

(22) Filed: Aug. 16, 2005

(51) Int. Cl.
*A01H 5/00* (2006.01)

(52) U.S. Cl. ..... Plt./252

(58) Field of Classification Search ..... Plt./252
See application file for complete search history.

*Primary Examiner*—Wendy Haas
(74) *Attorney, Agent, or Firm*—Greenlee Winner and Sullivan PC

(57) ABSTRACT

A new and distinct cultivar of crapemyrtle, *Lagerstroemia indicia×L. fauriei,* which is characterized by very compact, mounded growth habit; reddish-purple foliage all growing season, which holds up well in heat and humidity; high leaf powdery mildew and *Cercospora* leaf spot resistance; pink flowers, not as profusely borne as other Gamad varieties.

2 Drawing Sheets

Botanical classification: *Lagerstroemia indicia×L. fauriei.*
Varietal denomination: 'Gamad IV'.

BACKGROUND OF THE INVENTION

The present invention relates to a new and distinct cultivar of the ornamental flowering shrub *Lagerstroemia indicia× Lagerstroemia fauriei,* commonly known as crapemyrtle, and hereafter referred to by the varietal denomination 'Gamad IV'.

The new crapemyrtle originated from open-pollinated seed of 'Pocomoke' (unpatented) a compact, rose-pink flowered introduction in 1999.

1,017 seedlings were evaluated from 1999 for compact habit and year long reddish-purple foliage. 'Gamad IV' was selected as a single plant by the inventor in the summer of 1999 at Dearing, Ga.

SUMMARY OF THE INVENTION

Plants of the cultivar 'Gamad IV' have not been observed under all possible environmental conditions. The phenotype may vary somewhat with variations in environment such as light-intensity, temperature and cultural conditions, however, without any variance in genotype.

The following characteristics have been consistently observed and, to the best knowledge of the inventor, their combination form the unique characteristics of 'Gamad IV' as a new and distinct cultivar.

1. The most compact, mounded habit.
2. Reddish-purple leaves from emergence to leaf drop.
3. High leaf mildew, *Cercospora* leaf spot and flea beetle resistances.
4. Sparse pink flowers.

Plants of the new crapemyrtle have been compared to the parent 'Pocomoke'. Comparative evaluations in containers and in the ground at Athens, Ga., showed that 'Gamad IV' differed from 'Pocomoke' in the following characteristics:

1. Plants of 'Gamad IV' were considerably more compact than 'Pocomoke'.
2. Plants of 'Gamad IV' have reddish-purple foliage throughout the growing season.
3. Plant of 'Gamad IV' maintained cleaner, i.e. less diseased and flea beetle injured foliage than 'Pocomoke', into late October.

Asexual reproduction via tissue culture micropropagation and by traditional vegetative cuttings since the summer of 1999 has shown that the unique characteristics of this new crapemyrtle are stable and reproduced true-to-type in successive generations.

BRIEF DESCRIPTION OF THE PHOTOGRAPHS

The accompanying colored photographs illustrate the unique characteristics of the new cultivar, showing the colors as true as it is reasonably possible to obtain in colored reproductions of this type. Colors in the photograph may differ from the color values listed in the detailed botanical description which accurately describe the colors of the new crapemyrtle.

Figure 1:
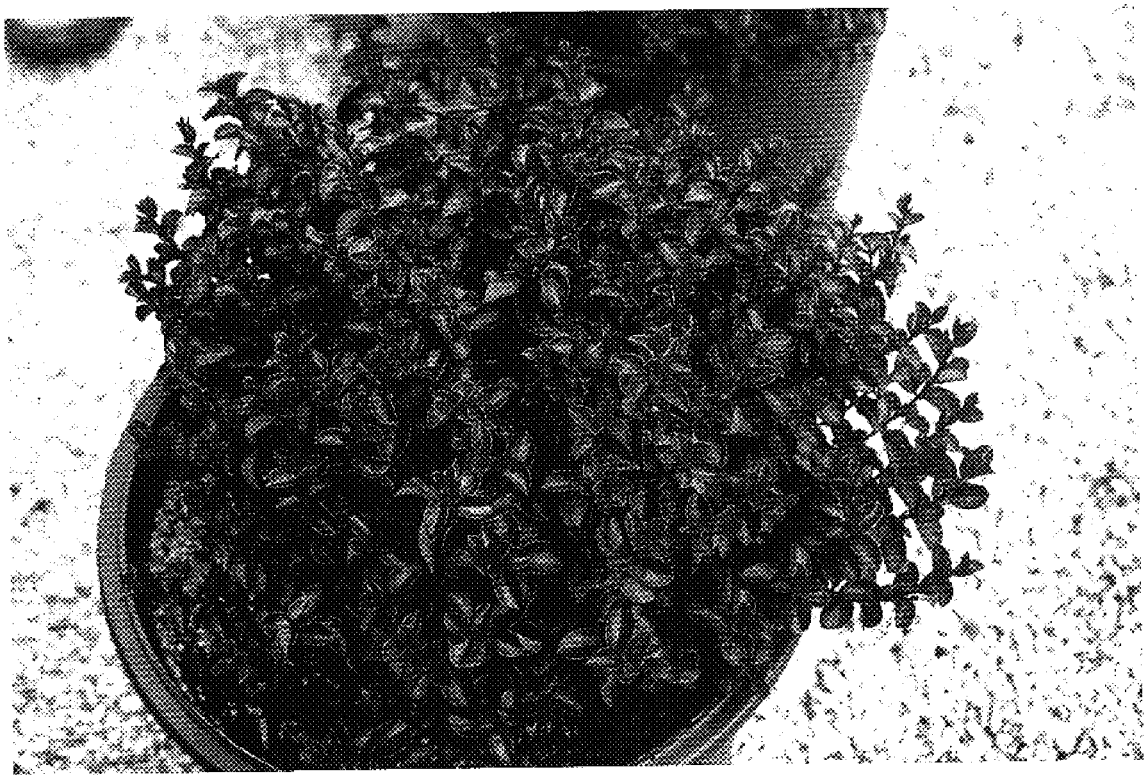

FIG. 1. A one-year-old plant growing in an 11.8 liter container in full sun in Athens, Ga. The picture was taken in the summer of 2003.

Figure 2:
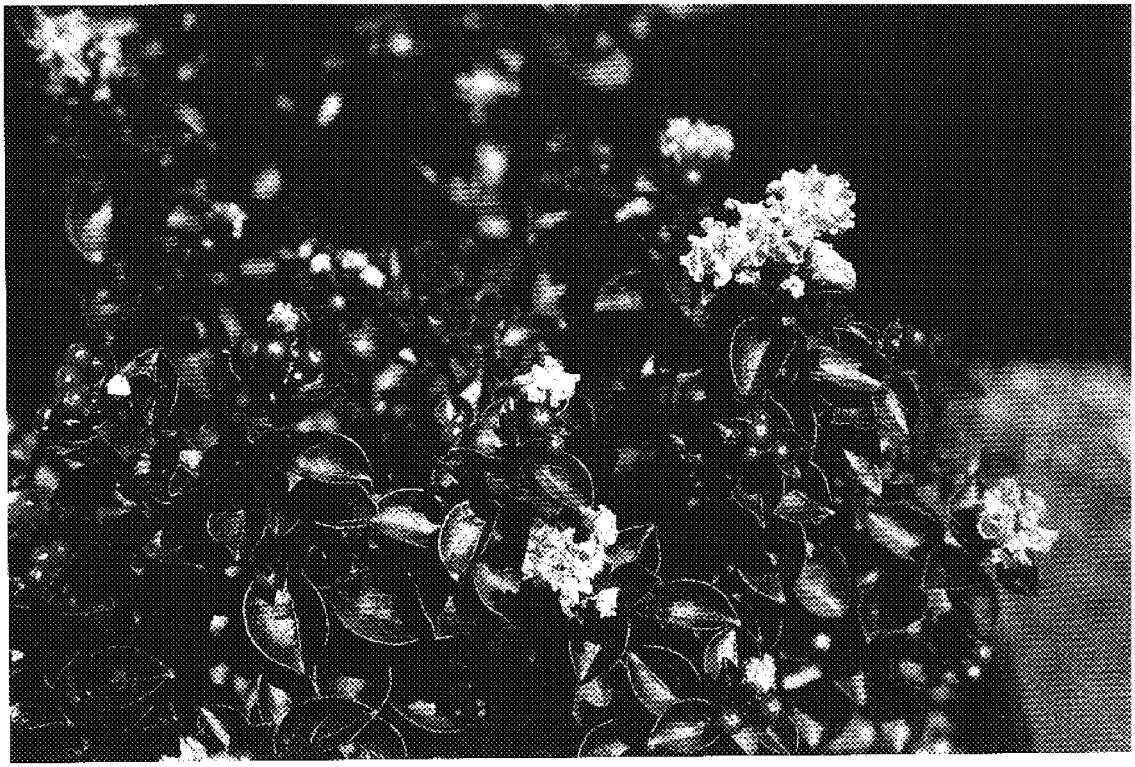

FIG. 2. The flowers on a one-year-old plant, taken in late summer of 2003.

DETAILED BOTANICAL DESCRIPTION

The botanical description of 'Gamad IV' is based on three-year-old plants, growing in 22 liter containers in an outside nursery research facility in Athens, Ga. (USDA Zone 7b) under conditions which closely approximate commercial production. Measurements are based on the average of 10 to 20 samples, and were taken throughout the main growth period, from March through September in Athens, Ga. Colors are based on The Royal Horticultural Society Chart, 1995 edition.

The plant has a compact, broad-mounded growth habit with medium texture and extensive branching, attaining an average height of 51 cm and width of 105 cm.

First year stems are squarish, turning oval down the stem, 1.5 mm in diameter halfway down the stem, with average internode length of 7.4 mm in the middle of the stem.

They are Greyed-Orange 166A in color, and the bark is exfoliating in strips except at the tip of the stem.

Second year stems are 5 mm in diameter, with color Greyed-Orange 166A, exfoliating to reveal Greyed-White 156A. The bark exfoliates in strips.

The vegetative buds are opposite to sub-opposite in arrangement, imbricate and conical in shape, 2 mm in length and 1 mm in width, with no pubescence, and the bud scales are Greyed-Orange 166A in color.

Mature stems are up to 25 mm in diameter, exfoliating Greyed-White 156A to Orange-White 159A.

The mature leaf, measured in the middle section of first year stems, averages 26 mm in length and 20 mm in width.

The leaf is ovate-elliptical, with an acuminate apex, rounded base and entire margin. The emerging leaf (April in Athens, Ga.) is Purple N77 on the upper surface and Greyed-Purple 187A on the lower surface. In summer (August), the upper surface is Green 139A and the lower surface is Yellow-Green 147B, with Purple N77margin.

The leaves are 0.5 mm thick and are arranged opposite to sub-opposite on the stem, with very shiny upper and semi-shiny lower surfaces. The venation is pinnate and the vein color is Yellow-Green 145D on upper surface and Red 39C on lower surface. The petiole is 1.5 mm in length and 1 mm in diameter, oval in cross-section shape with fine pubescence and Greyed-Red 178A in color.

The flower buds are 4 mm in length and 5 mm in width, round in shape with no pubescence, and are Greyed-Red 180B (immature) and Greyed-Red 179A (mature) in color.

The flowering period is from August to September in Athens, Ga.

The inflorescence is small, with 2 to 5 flowers.

The flower averages 14 mm in length and 22 mm in width. The color at emergence is picotee, White N 155B with Red-Purple N 66D, Red-Purple 68A in full bloom, fading to Red-Purple 63B.

There are 5 to 6 petals per flower, with an average petal size of 8.4 mm by 10.6 mm.

The sepals are Greyed-Orange 176C outside and Yellow-Green 145D inside.

The pedicels are 2.5 mm long, and are Greyed-Red 182A in color.

There is an average of 28 stamens, Yellow-Orange 14A in color. The filaments average 9.5 mm in length and are colored Red 36A.

The superior pistil with the style averages 7.3 mm in length, and is Greyed-Yellow 160C in color. The stigma is Yellow-Green 148A in color. There is a single ovary, averaging 2 mm in diameter and Greyed-Yellow 160B in color.

The mature fruit is a six-valved dehiscent, broad ellipsoidal capsule, measuring 6 to 8 mm in length and 6 to 8 mm in width, prior to dehiscence. The color is Brown 200A. There are multiple seeds per capsule, averaging 6 mm long, and 3 mm wide, with a membranous wing. The color of the seed is Brown 200A, and the wing is Grey-Brown 199D.

I claim:

1. A new and distinct cultivar of crapemyrtle plant named 'Gamad IV', substantially as illustrated and described.

* * * * *